United States Patent [19]

Lemchen

[11] Patent Number: 5,011,405

[45] Date of Patent: Apr. 30, 1991

[54] METHOD FOR DETERMINING ORTHODONTIC BRACKET PLACEMENT

[75] Inventor: Marc S. Lemchen, New York, N.Y.

[73] Assignee: Dolphin Imaging Systems, Valencia, Calif.

[21] Appl. No.: 301,606

[22] Filed: Jan. 24, 1989

[51] Int. Cl.$^5$ ............................................... A61C 3/00
[52] U.S. Cl. ...................................... 433/24; 433/229
[58] Field of Search ...................... 433/24, 72, 76, 223, 433/229

[56] References Cited

U.S. PATENT DOCUMENTS

| | | | |
|---|---|---|---|
| 3,949,478 | 4/1976 | Schinhammer | 433/24 |
| 4,014,096 | 3/1977 | Dellinger | 433/24 |
| 4,837,732 | 6/1989 | Brandestini et al. | 433/223 |
| 4,850,864 | 7/1989 | Diamond | 433/24 |

*Primary Examiner*—Cary E. Stone
*Attorney, Agent, or Firm*—Robert R. Thornton

[57] ABSTRACT

A method for determining orthodontic bracket placement on a malocclused tooth to correct the malocclusion includes the steps of generating digital information which defines the shape and location of the malocclused tooth in the patient's jaw, from which digital information a mathematical model of the tooth and jaw is generated. The correct placement position of a bracket is then calculated from the digitized information. A standard bracket is thereafter modified, if desired, individually for the patient, in view of the patient's physical deviations from the statistical averages. The shape of a bracket positioning jig is calculated and formed. Another step is forming an archwire for the brackets. The method may be used on one or more teeth in the same dental arch, as well as for both dental arches with respect to malocclusion therebetween.

19 Claims, No Drawings

METHOD FOR DETERMINING ORTHODONTIC BRACKET PLACEMENT

BACKGROUND OF THE INVENTION

Early in the history of orthodontics, doctors constructed their own appliances to treat patients. As the specialty grew, the orthodontic supply company became economically feasible. At first, all orthodontic brackets (braces), whether produced by the doctor or supply company, were designed simply as handles to which the force-producing agents, (most often archwires), were attached. Both the magnitudes and directions of orthodontic forces were controlled by placing appropriate bends in the archwires. See, for example, FIGS. 1 and 3 of U.S. Pat. No. 3,447,128.

The next major evolutionary step in appliance design was the "straight wire" concept. See, for example, FIGS. 2 and 4-19 of U.S. Pat. No. 3,477,128. Force magnitudes were still determined by wire and not the brackets. However, force vector directions were transferred from the wire to the brackets. Bracket slots were cut so that the desired forces were applied to each tooth in the arch by simply attaching (fully ligating) a straight length of wire with rectangular cross-section into the bracket slots. Futhermore, different bracket base thicknesses were employed to control labial-lingual dental positioning. See, for example, U.S. Pat. No. 3,660,900. These developments reduced considerably the amount of wire bending, and therefore, the doctor's chairtime required to treat a case. While such systems are generally considered to represent the state-of-the-art today, there remains a major disadvantage in the treatment mechanics of these products.

In the current "straight wire" systems, of which there are several, all bracket force vectors for specific tooth types (e.g., upper cuspids, upper central incisors, lower first molars, etc.) are manufactured to population averages. Thus, there is no individual adaptability in any given straight wire system. The patient's specific pretreatment malocclusion (condition requiring treatment), dental surface morphology, and facial type are completely disregarded. So, for that matter, are individualized treatment goals. It is well known, however, that these factors influence the selection of ideal mechanical parameters for every case. An orthodontic appliance placement method featuring parameters which are individualized is therefore a significant advance in the art over the present practice. The method of the present invention is utilized to provide for such appliance placement.

SUMMARY OF THE INVENTION

A method for determining orthodontic bracket placement on a malocclused tooth to correct the malocclusion includes the steps of generating digital information which defines the shape and location of the malocclused tooth in the patient's jaw, from which a mathematical model of the tooth and jaw is generated. The desired position of the tooth after treatment ("finish position") is determined.

In accordance with the particular method of orthodontic treatment which has been selected to be used on the patient by the practitioner, the correct position in which to place a bracket on the tooth to move the tooth to the finish position is then calculated from the mathematical model and finish position. The correct bracket position is defined as that position which yields zero force in all directions, if, and only if, the subject tooth is in its ideal position with the archwire installed. Thus, when brackets are placed and fixed in the patient's mouth, an archwire is placed on the bracket slots, and the archwire is fully ligated, the resultant individual force vectors will automatically move the teeth to the finish position.

The particular orthodontic bracket to be used in the present method may be selected either before or after calculating its placement position on the tooth. In either event, in the preferred embodiment of the method, the standard bracket is thereafter modified, if desired, so as to provide for tooth movement to the finish position which has been determined individually for the patient, in view of the patient's physical deviations from the dental and skeletal statistical averages for an ideal finish position.

Precise fixation of the brackets at the prescribed location in the patient's mouth is necessary for the proper corrective forces to be achieved. A further step in the preferred embodiment of the invention is to calculate the shape of a positioning device, such as a bracket positioning jig, for the orthodontic appliance to provide for the positioning of the bracket on the tooth in precisely the calculated placement position, and forming a positioning jig to conform to the shape of the jig so calculated. When the positioning jig with the bracket attached is placed over the patient's tooth, the bracket is automatically located at the precise position which will result in the required force vectors for treatment when attached to the tooth.

The forces to effect treatment are produced by the archwires. The archwires, when installed, act as springs which have been deflected by an amount proportional to the deviation of the tooth from its ideal location. An archwire, preformed in accordance with the requirements to move the affected tooth to its finish position when attached to the bracket, produces appropriate force magnitudes at various stages of treatment to move the tooth to its ideal position. An additional step in the preferred embodiment is the step of forming an archwire with respect to the mathematical model and the bracket into the configuration to cause to tooth to move to the calculated finish position when installed in the bracket on the tooth.

DETAILED DESCRIPTION OF THE PREFERRED EMBODIMENT

While normally the orthodontic treatment to be undertaken subject to the present invention will contemplate realignment of the patient's teeth in one or both arches, or even one arch with respect to the other, the method, for purposes of clarity and brevity of description, will be described with respect to the repositioning of a single malocclused tooth. The first step of the method of the present invention is the generation of accurate digital information defining the shape and location of the malocclused tooth with respect to the patient's jaw. This information may be generated in a number of ways, such as electromechanically, by laser scanning, sonic ranging, digital video scanning or magnetically. Various devices which may be so utilized are described in Rekow, *Computer Aided Design And Manufacturer In Dentistry: A Review Of The State Of The Art*, 58 The Journal of Prosthetic Dentistry 512 (1987). Sonic ranging devices of this type are described, for example, in U.S. Pat. No. 3,821,469.

The second step of the preferred embodiment is the generation of a mathematical model, utilizing the digitized information. The use of digitized information to generate mathematical models is well known in the Computer-Aided Design ("CAD") art, and need not be described at the present time in view of the state of the art. It should be noted that each of the three systems described in the Rekow article previously referred to uses CAD.

The mathematical model may be as detailed as the particular circumstances require, dependent only upon the quantity of digitized information generated in the prior step. Thus, in many applications of the preferred embodiment, a complete "model", as that term is used in the dental art to refer to a full replication of the upper and lower dental arches and associated jaw structure, will be mathematically generated. A physical embodiment of such a model is shown, for example, in FIG. 1 of U.S. Pat. No. 2,467,432.

The next step in the present method is the calculation of the "finish" position of the malocclused tooth or teeth, with respect to their positions in the mathematical model. Movement to the finish position typically may involve "tipping", that is, movement toward or away from adjacent teeth, "torquing", that is, angulating toward or away from the center of the mouth, and "rotation", that is, rotary movement of the tooth about its longitudinal axis, intrusional-extrusional or bodily movement.

There are a number of methods of treatment commonly used by the orthodontist. Each method takes different factors into account with varying degrees of emphasis. As utilized in the present invention, the orthodontist provides a description of the desired results, which is prescribed for reaching the finish position of each individual tooth relative to adjacent teeth, opposing teeth, supporting bony foundations and soft tissue, and the entire cranial-facial complex. Utilizing standard statistical tooth position data, the repositioning of the teeth is calculated to provide a mathematical model of the finish position. In the prior art, a similar step was accomplished manually in order to account for individual tooth morphology by physically removing duplicated teeth from a model and repositioning them in a new model in the finish position. See, for example, FIG. 3 in the above referenced U.S. Pat. No. 2,467,432. However, this procedure did not take into account the individual finish position desired relative to the cranial-facial base.

In the present method, this repositioning is done mathematically by appropriate software programs which may be derived by conventional means for the particular method of treatment elected by the orthodontist. An "ideal" finish position is not based upon statistical averages and takes into account the variation and physical characteristics of the individual patient. Therefore, it is preferable that, the program be utilized to provide a customized finish position for the particular patient, so as to make the finish position ideal for the patient, rather than attempting to have the patient duplicate the statistically average finish position.

After the finish position for the teeth in question has been calculated, the placement position of the orthodontic appliance, a bracket, for example, is calculated. In the presently preferred embodiment, a straight wire technique is utilized. The bracket manufacturers provide positioning information recommendations as to their brackets in the ideal position. This information is utilized together with the mathematical model of the finish position to calculate the bracket placement position on the teeth, which is conventional practice.

While it is possible to position the brackets on the teeth in a variety of methods, in the preferred embodiment of the present invention, the step of calculating the shape of a bracket positioning jig from the mathematical model in order to insure that the bracket is accurately placed is undertaken. A large variety of positioning jigs are known in the art, and such devices extend from rather simple direct application devices, such as is shown in U.S. Pat. No. 3,686,762 to complex devices such as are shown in U.S. Pat. Nos. 4,160,322; 4,183,141 and 4,360,341, which conform in shape to and overlay the tooth itself. In its broadest sense, the term "bracket positioning jig" as used herein includes devices utilized in the "indirect" method of bracket application, such as is described in U.S. Pat. No. 4,160,322, to position simultaneously a plurality of brackets on the patients teeth. Thus, after the particular form of jig has been selected, the shape of the jig required to place the bracket or brackets in the previously calculated placement position or positions is calculated. Thereafter, in the preferred embodiment, the next step of the present invention is to form the positioning jig calculated in the previous step.

Inasmuch as the mathematical model of the arch has been calculated in the preferred embodiment, another step in the practice of the present invention which may be utilized is the preforming of an archwire for attachment to the bracket to conform to the orthodontic treatment to be undertaken. The particular details as to shape, size, and the like of the archwire are matters of choice of the orthodontist, depending upon the particular treatment and brackets involved, and normally one the subject of specification in the prescription, if that step is to be undertaken in the practice of the present invention.

Orthodontic brackets are manufactured to population averages. One method of creating individualized brackets is to cut custom bracket slots for each patient. The cost of that procedure is usually prohibitive. The computerized design method, according to the present invention, utilizes modification of the angulation of the bracket/tooth interface on an individualized basis in order to cause the bracket to produce a desired force vector on the tooth. Specific force vectors are prescribed, and an entire system of brackets/adhesive placement, pre-formed archwires, and peripheral appliances (head gear, elastics, etc.) is selected, if so desired.

In some instances in the practice of the present invention, a particular bracket may be selected and, for the particular case, modified in certain respects before calculating its placement position. In such an instance, the placement position is calculated for modified form of the bracket. In other instances, a selected bracket may, after calculation of its placement position, be determined to require modification in order to be placed in the required placement position. In such an instance, the present invention contemplates the modification of the bracket after calculation of the placement position to prevent its placement in accordance therewith.

In the method of the preferred embodiment, standard brackets are modified as appropriate to produce the required treatment force vectors by use of a structural adhesive system. The modification of standard brackets by use of a structural adhesive system is known in the art. The structural adhesive is initially a moldable putty which easily takes on the contour of the dental surface to which the appliance will be fixed, and which provides the interface between that surface and the bracket base. A premachined archwire slot in the bracket face can thus be oriented with six axes of freedom with respect to the dental surface so as to incorporate precisely the required force vectors. In practicing one embodiment of the present one that, the bracket is correctly positioned on a laboratory model of the tooth, and the adhesive is hardened to a rigid state by a irradiation with ultraviolet light, followed by oven post-cure. The adhesive is then an inseparable, integral part of the bracket, now customized for that patient's individual tooth.

While the use of a moldable putty to interface between the bracket and the tooth is satisfactory, the present method may be utilized in conjunction with computer-aided design and computer-aided manufacturer (CAD/CAM), as described in the Rekow article referred to above, to provide a machined or cast base conforming to the tooth morphology and containing an appropriately positioned bracket receiving recess or fitting, so as to permit the base to be fixed to either the bracket or the tooth. The other of the two is then fixed to the base, thereby simplifying the attachment of the bracket to the tooth and its customized ideal position for the individual patient. By this method, standard brackets are readily adapted to customized use, so as to simplify the inventory retirements of the practitioner. Additionally, such customized brackets may be provided to the practitioner by a dental laboratory, where the digitized information is utilized in the process of providing the practitioner with the required dental appliances for the correction of the malocclusion.

As will be apparent, the practice of the present invention may be restricted to a single tooth, may be utilized with some or all of the teeth in a given dental arch, or utilized with teeth in both of the arches of the patient. Therefore, while the description of the practice of the invention has been stated, in certain instances, with respect to a single tooth for purposes of brevity and clarity, the practice of the invention is not so limited.

Furthermore, the present invention may also be utilized with respect to orthodontic diagnoses involving the requirement of movement of one arch, in its entirety, with respect to the other, as where the patient exhibits a lateral offset. In such an instance, a mathematical model is calculated for both arches in their relative positions with respect to one another. The preferred embodiment takes into account the relative resistance to movement of various teeth or groups of teeth. Bracket positions are customized to account for these forces. Indications are provided for the inter-dental arch force mechanics in order to correct or maintain the position of each individual arch over its respective jaw structure as well as relative to the opposing arch and jaw.

I claim:

1. A method for determining orthodontic bracket placement on a malocclused tooth in a patient's jaw to correct the malocclusion comprising the steps of:
    generating digital information defining the shape and location of the malocclused tooth with respect to the patient's jaw;
    generating a mathematical model of the malocclused tooth as positioned in the jaw from the digitized information;
    calculating the finish position in the jaw to which the malocclused tooth is to be moved from the digitized information; and
    calculating the placement position of an orthodontic bracket on the malocclused tooth required in order to move the malocclused tooth to its finish position by a preselected orthodontic treatment.

2. The method of claim 1, and including the step of selecting the orthodontic bracket to be utilized before calculating its placement position.

3. The method of claim 2, and including the step of modifying the selected orthodontic bracket after calculating the placement position to improve its performance in moving the malocclused tooth to its finish position.

4. The method of claim 2, and including the step of modifying the selected bracket before calculating its placement position.

5. The method of claim 1 and including the step of selecting the orthodontic bracket to be utilized after calculating its placement position.

6. The method of claim 5, and including the step of modifying the selected orthodontic bracket after calculating the placement position to improve its performance in moving the malocclused tooth to the finish position.

7. The method of any of claims 1, 2, 5, 3, 4, or 6 and including the step of calculating the shape of a bracket positioning jig for the malocclused tooth required in order to place the respective tooth bracket in the previously calculated placement position.

8. The method of claim 7, including the step of forming a bracket positioning jig to conform to the bracket positioning jig shape previously calculated.

9. The method of claim 8, and including the step of preforming at least one archwire for attachment to the selected bracket into such configuration with respect to said bracket as is to be utilized to cause the malocclused tooth to move toward its finish position when the bracket is fixed to the tooth in the placement position and the archwire attached thereto.

10. A method for determining orthodontic bracket placement on a dental arch to correct a malocclusion comprising the steps of:
    generating digital information defining the shape and location of the teeth with respect to the arch;
    generating a mathematical model of the teeth as positioned in the arch from the digitized information;
    calculating the finish position in the arch of the teeth from the digitized information; and
    calculating the placement position of orthodontic brackets on selected teeth in the arch required in order to move malocclused teeth to their finish positions by a preselected orthodontic treatment.

11. The method of claim 10, and including the step of selecting at least one of the orthodontic brackets to be utilized before calculating its placement position.

12. The method of claim 11, and including the step of modifying at least one of the selected orthodontic brackets after calculating its placement position to improve its performance in moving a malocclused tooth to its finish position.

13. The method of claim 11, and including the step of modifying at least one of the selected brackets before calculating its placement position.

14. The method of claim 10 and including the step of selecting at least one of the orthodontic brackets to be utilized after calculating its placement position.

15. The method of claim 14, and including the step of modifying at least one of the selected orthodontic brackets after calculating the placement position to improve its performance in moving the malocclused tooth to the finish position.

16. The method of any of claims 10, 11, 14, 12, 14, or 15, and including the step of calculating the shape of a bracket positioning jig for use in placing the brackets in their previously calculated placement positions.

17. The method of claim 16, including the step of forming a bracket positioning jig to conform to the bracket positioning jig shape previously calculated.

18. The method of claim 17, and including the step of preforming at least one archwire for attachment to the brackets into such configuration with respect to said brackets as is to be utilized to cause the teeth to move toward their finish positions when the brackets are fixed to the teeth in their placement positions and the archwire attached thereto.

19. A method for use in the orthodontic treatment to correct the malocclusion between teeth in a patient's dental arches comprising the steps of:
   generating digital information defining the shape and location of the teeth in each dental arch with respect to the other dental arch;
   generating a mathematical model of the dental arches as positioned in the patient's head from the digitized information;
   calculating the finish position of the dental arches which is required to correct the malocclusion from the digitized information; and
   calculating the placement position of an orthodontic appliance on at least one of the arches required in order to correct the malocclusion by a preselected orthodontic treatment.

* * * * *